United States Patent [19]

Prussin

[11] 4,278,206

[45] Jul. 14, 1981

[54] NON-PRESSURIZED DISPENSING SYSTEM

[75] Inventor: Samuel B. Prussin, Big Sur, Calif.

[73] Assignee: AE Development Corporation, Minneapolis, Minn.

[21] Appl. No.: 29,630

[22] Filed: Apr. 13, 1979

[51] Int. Cl.[3] .............................................. B05B 11/04

[52] U.S. Cl. ...................................... 239/327; 222/215

[58] Field of Search ................ 239/327; 222/206, 207, 222/211, 214, 215; 252/305, 308, 316; 424/46, 47

[56] References Cited

U.S. PATENT DOCUMENTS

| | | | |
|---|---|---|---|
| 3,140,052 | 7/1964 | McCuiston | 239/327 |
| 3,488,002 | 1/1970 | Mina | 239/327 |
| 4,015,753 | 4/1977 | Bennett | 239/327 X |

*Primary Examiner*—Andres Kashnikow

*Attorney, Agent, or Firm*—Marvin E. Jacobs

[57] ABSTRACT

A water-in-air emulsion or suspension containing a dispensible material is formed by stabilization of small droplets of aqueous liquid with an interfacial barrier of very fine, hydrophobic metal oxide particles such as silane modified silica. As the droplets are subjected to shear such as during passage through an orifice, the shear forces experienced partially destabilize the barrier allowing the droplets to coalesce to form particles of controlled density and increased size. At least 10% of the droplets coalesce into particles after leaving the orifice. Active ingredients such as antiperspirants may be added to either the aqueous liquid phase or to the powder phase as long as they do not destabilize the suspension. A non-pressurized system comprises a container suitable for dispensing the suspension having a compartment receiving the suspension, a valve having an outlet orifice of a dimension adapted to impart a preselected shear and destabilization to the suspension and the container being adapted to enable the suspension to be propelled through the outlet orifice.

23 Claims, 4 Drawing Figures

NON-PRESSURIZED DISPENSING SYSTEM

DESCRIPTION

1. Technical Field

The present invention relates to the dispensing of materials from a container and, more particularly, to a novel water droplet-in-air suspension and system for dispensing such materials.

2. Background Art

Pressurized dispensing systems, commonly referred to as aerosols, experienced first significant commercialization in the early 1950s resulting in a proliferation of products. Basically, however, most pressurized products have the following elements in common:

a. A container suitable to withstand the pressure of the system;

b. A propellant of either the liquefied or compressed gas types;

c. A valve means across which there is a pressure drop to ambient pressure and which directs the product in the form of a spray or foam to the target area.

Despite their high costs, aerosol products gained immediate consumer acceptance. By the mid-1970s the dollar volume domestically approached $2.5 billion with worldwide sales about twice that figure.

The single most important factor behind this success story is the convenience offered by these pressurized products. Entire product categories changed overnight: shaving products in tubes gave way to preformed foams; forms of hair fixatives other than hair sprays disappeared from the market; roll-on antiperspirants were displaced by their non-contact and drier but less effective spray counterparts.

Typically, aerosols are generated by atomization of the composition through a valve. The atomization pressure is generated by a propellant in either gaseous or liquefied form, typically, low molecular weight liquid halohydrocarbon or hydrocarbon propellants or gases under pressure such as nitrous oxide, carbon dioxide or nitrogen.

Recently, the aerosol market was thrown into a state of disarray as a result of the Rowland-Mollina ozone depletion theory which hypothesizes that a certain percentage of halohydrocarbon propellants find their way to the stratosphere causing a depletion of ozone in that stratum. With a depletion of the ozone in the stratosphere, a greater amount of ultraviolet radiation enters the atmosphere resulting in an increased incidence of skin cancer. The Federal Government has taken steps to ban the production and sales of halohydrocarbon propellants, and the sales of halohydrocarbon propelled products with minor exceptions will no longer be permissible after the first quarter of 1979.

Packaging alternatives to halohydrocarbon propelled aerosols include: products propelled with liquefied hydrocarbon propellants (LPG) such as butane, isobutane and propane and mixtures thereof. Because of the flammability of the LPG gases a substantial amount of water is necessary in the formulation to provide a dousing effect. Aqueous phases emulsified in hydrocarbon propellants (water/oil) can yield fine space sprays and are currently used for room deodorants, insect sprays, and the like. Products propelled with compressed gas propellants such as nitrogen or the more soluble nitrous oxide and carbon dioxide are usually quite wet because their low solubilities and low concentrations (as compared with halohydrocarbon and hydrocarbon propellants) deprive the produce of breakup power. Combinations of liquefied and compressed gas propellants offer no synergistic advantage in terms of achieving a dry spray.

Surprisingly, antiperspirant suspensions comprising nearly 100% flammable hydrocarbon propellant as the suspending vehicle and driving force are now being marketed. Such products deliver a dry spray but are very flammable. To partially decrease this risk, the spray rate of these products has been decreased. Furthermore, hydrocarbon propelled solutions of antiperspirant aerosols containing alcohol and water delivered a spray that was much wetter than the comparable fluorocarbon suspensions and did not receive consumer acceptance.

There are, also, the ever-present dangers of aerosols: flammability (in the case of hydrocarbon propelled products), explosion hazard, inhalation toxicity potential, inadvertent misuse of product, valve malfunction, etc.

Pump sprays are high cost, low efficiency substitutes for pressurized products. Hair fixatives and antiperspirant pump sprays are currently on the market as non-aerosol counterparts. Their acceptance, especially the antiperspirant pump spray, has been poor primarily because of the wetness of the application.

Other packaging forms including separative devices, elastomeric membranes with a memory, spring loaded devices, etc., are of little commercial value because of the inordinately high cost, the exotic nature of the hardware and the lack of basic improvement over existing lower cost systems.

Hydrophobic metal oxides, particularly silane treated silicas, were developed about ten years ago. Hydrophobic metal oxides are not wetted by water. Currently, the hydrophobic metal oxides are used to prevent wetting by water such as in sands, soils and other granular materials or surface treatment of masonry, wood, cloth, paper, plastic and other surfaces. The hydrophobic metal oxides also find use as a free-flow anti-caking additive in powder fire extinguishers, polymers, metals, etc.; as a thickening and anti-settling agent with waterproofing characteristics in paints, adhesives, greases, inks and similar systems and as a polymeric reinforcing agent. In practice the hydrophobic metal oxides are finding use as colloidal surface active agents in high viscosity water-in-oil emulsions having exceptional phase stability for use in insecticides, creams and salves. Vigorous mixing of hydrophobic metal oxide and water results in a water-in-air emulsion or suspension in which fine droplets of water as a first phase are stabilized in air by an interfacial barrier of very fine hydrophobic metal oxide particles. U.S. Pat. No. 3,393,155, Col. 5, lines 2–3 discloses that aqueous solutions of substances such as glycerol can be used in the aqueous disperse phase for addition to pharmaceuticals or cosmetics. The only commercial use of water-in-air emulsions based on hydrophobic silica as a free flowing powder is as a fluffy bed for germination of hard-to-grow seedlings. (U.S. Pat. No. 3,710,510)

The hydrophobic metal oxides can be applied to surfaces by blending or dusting. Coating formulations can be formulated with resin binders in liquid state or dry state and these coatings have been applied by spraying, fluidized bed or electrostatic coating techniques or by a containerized propellant. However, these applications do not involve liquid-in-air emulsions nor the use of such emulsions to deliver ingredients to a target as an aerosol.

Aerosols are formed by the dispersion of fine particles in air. However, antiperspirant sprays delivering fine particles having a diameter smaller than 10 microns are inhalable and should be reviewed for long term toxicity effects to assess the risk/benefit balance in allowing the public to use such products. Conversely, particles having diameters larger than 10 microns are removed in the trachea and do not entail significant risk in their use. The particles delivered from conventional propellant or pump spray packages decrease in size as they travel to a target tending to shift the particle size to an inhalable range.

STATEMENT OF INVENTION

It has now been discovered in accordance with this invention that the propulsion of liquid-in-air suspensions of hydrophobic metal oxide stabilized liquid droplets through an orifice results in the partial destabilization of the interfacial barrier and formation of coalesced particles of increased diameter caused by the shear forces experienced in passing through the orifice. The coalesced particle size can be controlled to be larger than the minimum sized particle than can be inhaled, preferably so that inhalation risks are minimized. It has further been discovered that bio-affecting or cosmetic ingredients such as antiperspirant or personal deodorant compounds can be added to the powder or aqueous phase of the bulk liquid-in-air emulsion or suspension without affecting the ability to form the containerized bulk liquid-in-air suspension or to dispense the coalescing particle.

Whereas, propellant aerosol or pump sprays must have small particle size and must have little or no water or alcohol to deliver a dry application, the system of the present invention can have a large particle size and can contain substantial amounts of water (60–70%) and still dry quickly.

It is surprising that the substantial amount of water in the formulation of the invention does not deter the quick dry out of the dispensed material. Furthermore, alcohol can be present in the suspension without contributing a sensation of wetness. Another salient difference between pressurized aerosols and pump sprays and the system of the invention is that with the former products, the particle size decreases from valve to the target whereas with the products of this invention the particle size increases from valve to target.

A non-pressurized dispensing system of the invention comprises a container having a compartment receiving the hydrophobic metal oxide-stabilized aqueous droplet suspension, a valve having an outlet orifice of a dimension adapted to impart a preselected shear and destabilization to the suspension and the container being adapted to enable the suspension to be propelled through the orifice suitably by a pulse of gas. The container may contain means of introducing ambient air to supply the gas for dispensing the suspension through the orifice.

One embodiment of a dispensing system can comprise a resilient, flexible container having a compartment for receiving the bulk liquid-in-air suspension and a valve including a mixing chamber and having a vapor port, a means for feeding the suspension to the mixing chamber, and an outlet orifice whereby on squeezing the container, vapor and suspension enter the mixing chamber, intermix therein and are expelled through the outlet orifice to form a suspension of powder encapsulated droplets that at least partially coalesce as they travel to the surface of the target. Other potential dispensing systems capable of imparting the requisite shear include pump sprays, pressurized dispensers of the bag or piston variety, etc.

The novel system of dispensing products in aerosol form in accordance with the invention utilizes a simple, inexpensive but highly functional, non-pressurized system. The system is capable of delivering a small particle in the aerosol range where the only propelling force is the finger pressure on a resilient plastic container; further, the spray may feel dry although the formula may, paradoxically, contain substantial amounts of water. Since the system contains this water, it permits the spray to be rubbed out as an elegant cream or lotion.

Whereas pressurized products such as antiperspirants and deodorants, hair sprays, shave foams, insecticides, fragrance items, inhalation therapy products, etc., comprise from 0.25% propellants in the case of insoluble compressed gases such as nitrogen and up to 90% propellants in the case of liquefied propellants, usually in the range of 20–80 psig, the products of the invention utilize air as the vehicle in a nonpressurized dispensing package. The largest selling aerosol category, for example, antiperspirant sprays, are generally suspensions of antiperspirant powders in a predominantly propellant vehicle; by comparison, the antiperspirant salts in the products of the invention are suspended in air (an air emulsion so to speak). Both product forms deliver a dry spray although the aerosol has, among other liabilities, an unpleasant cooling sensation.

It is important to emphasis that the products of the invention are not powders. Although existing in "powdery form" they differ from powders in virtually all respects; a more accurate description for the aqueous encapsulated vehicle component of the system is detailed in Table 1.

TABLE 1

| | Powder | Aqueous Encapsulation |
|---|---|---|
| SOLIDS | Principally solids in most cases; incapable of absorbing appreciable fluids and remaining particulate and free flowing. | Can contain up to 90% $H_2O$ and remain particulate and free flowing (actually a water in air emulsion). |
| PHYSICAL STATE | Powder | "Powdery Substance" with fluid properties. |
| PARTICLE SIZE | Fixed | Capable of being controlled in motion during dispensing and application. |
| DENSITY | Fixed | Capable of a wide range of adjustments; density can be altered during dispensing and application. |
| FORMULATION FLEXIBILITY | Very limited | Extremely broad |

TABLE 1-continued

| | Powder | Aqueous Encapsulation |
|---|---|---|
| TOPICAL APPLICATION | Slip and feel of talc at best | Can be dispensed as a dry spray (similar to an aerosol antiperspirant) or can be rubbed out as a cream or lotion, depending on product attributes desired. |
| DISPENSING CHARACTERISTICS | As a powder | As an aerosol or as a powder |
| SOLIDS LOAD | Approximately 10% maximum in aerosols before valve malfunctions. | No upper limit in non-pressurized dispensing system. |

The active ingredient may be dissolved in the aqueous phase, dispersed therein as an emulsion or suspension or added to the powder phase. Antiperspirant salts such as aluminum chlorohydrate can be added to either phase but a product with less sticky feel is produced by addition of this active agent to the powder phase. The system of the invention will also find use in dispensing other products such as cosmetics, personal deodorants, hair dyes, pharmaceuticals, and household products such as oven cleaners, insecticides, spot removing agents and the like.

The system of the invention provides good adhesion to target, non-occlusiveness, breathability, good coverage of target area, no build-up, is non-caking in the package and on the skin, has good slip properties, provides controlled cooling, is cosmetically elegant and is a safe, effective and economical product.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
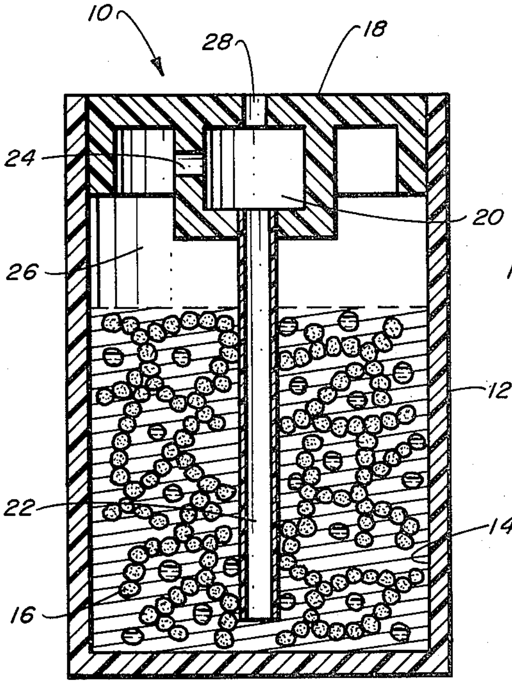
FIG. 1 is a schematic view of the container of the invention before dispensing.

Referring now to FIG. 1, an embodiment of the non-pressurized dispensing system of the invention can be a squeeze bottle 10 which generally includes a flexible container 12 suitably formed of a resilient synthetic organic resin such as medium density polyethylene having a lower chamber 14 receiving a charge 16 of the water-in-air emulsion or suspension containing an active ingredient. A valve 18 closes the top of the container 12. The valve 18 includes walls defining a mixing chamber 20. A dip tube 22 extends from the mixing chamber 20 into the charged material 16. A vapor port 24 comminucates with the air in headspace 26 and an outlet orifice 28 communicates with the surrounding environment.

Figure 2:
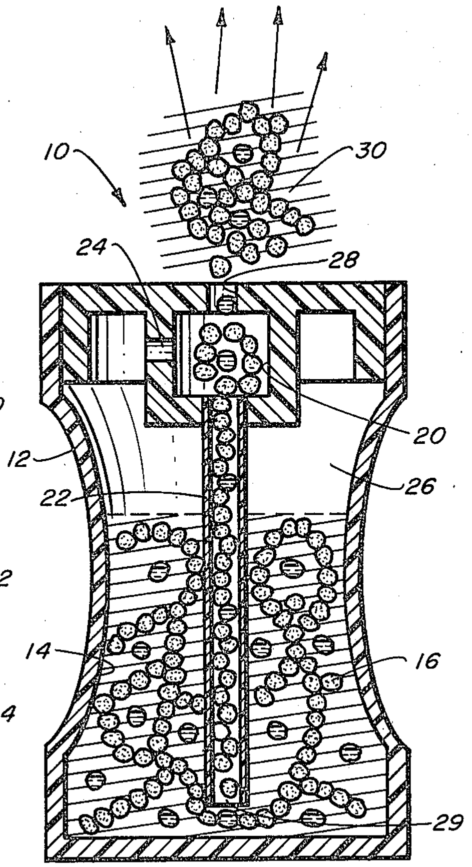
FIG. 2 is a schematic view of the container during dispensing.

Referring now to FIG. 2, when the container is manually squeezed by finger pressure, air is induced from headspace 26 through vapor port 24 into chamber 20 as the charged material 16 simultaneously passes through the lower opening 29 and up the dip tube 22 into the chamber 20. As finger pressure is released, the container recovers its memory and air is introduced into the headspace 26 through outlet orifice 28 and vapor port 24. It is apparent that if the diameter of the vapor port 24 and dip tube 22 are balanced, the product may be dispensed essentially in the same condition as in the upright position when the container 12 is in inverted position. Generally each pulse of the container will dispense from 40 mg to 300 mg, usually 75 to 150 mg, depending on the density of the water-in-air suspension or emulsion and the degree of shear desired.

The shear imparted to the dispensed charge is a direct function of the velocity of the material through the outlet orifice and an inverse function of the diameter of the outlet orifice.

Figure 3:
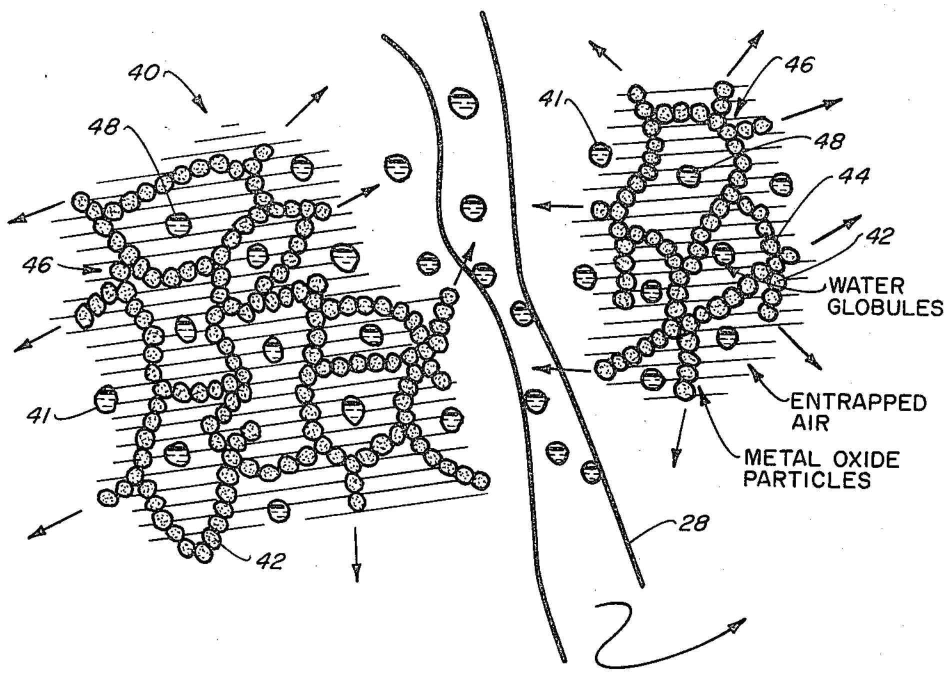
FIG. 3 is a schematic view of the microencapsulated aqueous phase.

FIG. 3 illustrates the microencapsulated aqueous phase 40. In the manufacturing process, the primary hydrophobic metal oxide particles 42 fuse together to form chained particles 44 which have a strong tendency to interact with each other to form a three dimensional network or lattice structure 46 encapsulating discrete water globules 48 with approximately seventy parts of air trapped in the void space. When the aqueous phase and the hydrophobic metal oxide are subjected to high shear mixing the aqueous droplets 48 are trapped in the three dimensional lattice structure, where air is the continuous phase of the dispersion. The air cushioned hydrophobic aggregates surround the small aqueous droplets preventing coalescence and stabilizing the system. When the shear potential is exceeded, such as during travel through the outlet orifice 28, the aqueous phase will coalesce in whole or in part. Total coalescence can occur on the target surface by rubbing the material on the body or by combing the product through the hair.

Optimum functioning of the system and delivery of the desired spray effect depends on the dispensed particle size and its density, the changing size and density of the particles in flight and on the target, the delivery rate, the degree of hydrophobicity and the nature of the application (dry, moist or creamy). Optimum functioning of the system also depends on the shear stability of the suspension which, in turn, is influenced by the following factors:

1. The ratio of the hydrophobic metal oxide to the aqueous phase;
2. The type of hydrophobic metal oxide used;
3. The amount and nature of the actives;
4. The amount and nature of the system affecting additives;
5. Processing techniques;
6. Delivery system parameters.

Synthesis of hydrophobic metal oxides by reaction of metal oxides and metalloid oxides, particularly colloidal silicas, with various organosilicon compounds has been rather extensively developed. Various organosilicon compounds bearing at least one functional moiety per molecule can be reacted through said functional moiety with the hydroxyl groups existing on the surface of the metal or metalloid oxides. The resulting reaction product is characterized as a metal oxide or metalloid oxide having chemically bonded to the surface thereof organosilicon groups represented generally by the formula:

$$eO—MR_aX_b$$

where e represents the oxide surface; O is oxygen; M is a metal or metalloid such as silicon, each R is any alkyl, aryl, arylalkyl, alkoxy or aryloxy group, a is a number from 1 through 3, X is any halogen or hydroxyl group, b is a number from 0 through 2, and $a+b=3$.

The organosilicon groups are introduced onto the surface of the metallic oxide in an amount sufficient to render the surface of the metal oxide hydrophobic. Generally, at least 50% of the available oxygen groups on the surface such as silanol groups are converted, typically about 70%. Hydrophobic, pyrogenic silica can be produced in accordance with the teachings of U.S. Pat. No. 3,393,155 or other patents such as U.S. Pat. Nos. 2,510,661, 2,589,705, 2,705,206, 2,705,222 and 3,023,181.

In preparing the dispersion of aqueous liquid in fine solid particulates for use in the present invention, in addition to or in place of the hydrophobic pyrogenic silicas used in U.S. Pat. No. 3,393,155, other strongly, hydrophobic metallic oxides having an average equivalent spherical diameter of less than about 100 millimicrons, typically from 1 to 20 millimicrons, can also be used. For example, other finely divided oxides such as aluminas, titanias, ziconias, vanadium oxides, iron oxides or mixed oxides with or without silica can form the basic oxide particles whether produced pyrogenically or otherwise, e.g., by wet precipitation techniques. Also, wet precipitated silicas such as those produced by acidification or neutralization of aqueous alkali metal silicate solutions make ideal starting materials when available in particulate form of the desired fineness. For example, U.S. Pat. Nos. 2,865,777, 2,900,348, 2,913,419, 2,995,422, 3,010,791, 3,034,913, 3,172,726, 3,208,823 and 3,250,594 describe a few of the many different techniques for precipitating particulate silicas from aqueous medium in a form which is sufficiently non-sticky and non-gelatinuous to be washed, filtered, dried and subdivided to colloidal powder form.

Specific examples of organosilicon compounds which are often reacted with colloidal metallic oxides to form surface structures like those described above are: organohalosilanes such as $(CH_3)_3SiCl$, $(CH_2)_2SiBr_2$, $(CH_3)_2SiCl_2$ and $(C_4H_9)_3SiCl$; organosilylamines such as $(CH_3O)_3Si(CH_2)_3—NH(CH_2)_2NH_2$ and $(CH_3O)_2(CH_3)SiCH_2CH(CH_3)—CH_2NHCH_2CH_2NH_2$; organodisilazanes such as $(CH_3)_3SiNHSi(CH_3)_3$ and $(C_4H_9)_3—SiNHSi(C_4H_9)_3$, etc. In most cases, the surface treatments must be sufficient to attach organo groups totaling at least 0.5 percent and preferably at least 1 percent by weight based on the dry weight of the metallic oxide particles treated. In many cases, especially with the most preferred high surface area oxides, the concentration of organo groups thereon will equal 2 percent or more by weight.

Examples of commercially available hydrophobic silicas are described in the following table.

TABLE 2

| Silica | Type | Source |
|---|---|---|
| QUSO WR50 | Wet Precipitation Process | Philadelphia Quartz |
| QUSO WR82 | Wet Precipitation Process | Philadelphia Quartz |
| Aerosil R 972 | Fumed Silica-Pyrogenic | Degussa |
| Tullanox 500 | Fumed Silica-Pyrogenic | Tulco Inc. |

The metal oxide starting materials contain substantial amounts of occluded air in a stable configuration. The air is retained in the hydrophobizing reaction resulting in a very low apparent density, i.e., as low as 0.06 g/cc; the real density of the hydrophobic metal oxides is about 2 g/cc. The density of the water-in-air emulsion can be from about 0.30 to 1.5 g/cc, generally from about 0.45 to 0.90 g/cc.

The pyrogenically produced metal oxides have more occluded air than do their precipitated counterparts and result in a lower density bulk. For any given system the pyrogenic material contributes considerably more shear resistance to the bulk than do precipitated metal oxides. Thus, if a more shear prone, moist to creamy application is desired, a precipitated metal oxide may be more desirable than the pyrogenic variety; conversely the pyrogenic metal oxide will provide a more shear resistant, drier application. Based on the number of controllable variables, however, each type of metal oxide can be formulated to yield the entire spectrum of application characteristics.

The ratio of hydrophobic metal oxide to aqueous liquid can be from 1/1 to 50/1, generally from 5/1 to 20/1. If the ratio of the hydrophobic metal oxide to water is high (all other factors being equal) the encapsulated aqueous base will be more shear resistant as a result of the mechanical crowding of the hydrophobic metal oxide at the aqueous/air interface and additional energy or scrubbing action will be required as the bulk passes through a given valve orifice to effect shear (if such is desired) resulting in the coalescence or partial coalescence of the aqueous phase with an increase in both particle size and density; conversely, if the ratio of hydrophobic metal oxide to the aqueous phase is low, the bulk will be more shear prone as it passes through the valve orifices. For any given system the physical properties will be least affected when the valve orifices are sufficiently large to have a minimal influence on the shearing of the bulk. Shear and its consequence, coalescence, results in an increase in both particle size and density, both in flight and on the target area.

Formulations useful in the present invention normally contain 1-15% by weight of hydrophobic metal oxide, 25 to 98.9% by weight of water and 0.1 to 60% by weight of dispensible material.

Processing is vital to achieving the desired degree of shear resistance for a given valve system. The minimum amount of mixing to form the water-in-air dispersion will provide the greatest degree of shear stability when the bulk passes through a given valve orifice. As mixing continues the bulk loses its shear resistance, and at a certain, well-defined, consistent amount of mixing the suspension will collapse to form a totally coalesced creamy material. Processing is also a function of the type of hydrophobic metal oxide used. Pyrogenic hydrophobic metal oxides will tolerate substantially more shear than identical systems made with precipitated hydrophobic metal oxides. Generally, the preblended solids are added to a vortex of the liquids in a high speed mixer such as a blender and mixed for 1 to 600 seconds, generally 5 to 300 seconds. Alternatively, the pre-blended powders and aqueous liquid phase are combined and then blended as above.

The system of the invention will now be illustrated by the following examples which are presented for purposes of illustration and not limitation of the invention.

EXAMPLE 1

| Ingredient | % Weight/ Weight (W/W) |
|---|---|
| Aluminum Chlorohydroxide, Impalpable Powder | 25 |
| Hydrophobic Silica | 4-6 |
| Zinc Stearate | 4 |
| Water | 67-65 |

Various hydrophobic metal oxides were utilized to prepare antiperspirant formulations in a blender having 14 variable speeds.

The following trends and discussions evolve from examining the data:

(1) Tullanox 500, 4%, 5% and 6%

(a) Increasing the concentration of Tullanox 500 (all other factors remaining equal) permits longer blending times, irrespective of powder blending speeds. With higher concentrations of Tullanox 500, more stabilizing particles exist in the aqueous/air interface requiring commensurately additional energy for disruption of the system and coalescence of the aqueous phase resulting in increased density.

(b) The density is an inverse function of the Tullanox 500 concentration. The higher Tullanox 500 concentration not only results in a more air stable configuration, but also, because of its low apparent density of 0.06 grams/cc directly affects the density of the system. This is evident from the examples given below:

| | (1) 10% Tullanox 500 | | |
|---|---|---|---|
| | % W/W | Density | CC/100 Grams |
| Tullanox 500 | 10 | 0.06 | 167 |
| Water | 90 | 1.00 | 90 |

The theoretical density of the 10% Tullanox 500 system: $d=100/257=0.39$ g/cc.

| | (2) 5% Tullanox 500 | | |
|---|---|---|---|
| | % W/W | Density | CC/100 Grams |
| Tullanox 500 | 5 | 0.06 | 83 |
| Water | 95 | 1.00 | 95 |

The theoretical density of the 5% Tullanox 500 system:

$d=100/178=0.56$ g/cc

Thus, with an increase of Tullanox from 5% to 10% the density of the system is reduced by about one-third.

(c) Higher batch blending speeds, irrespective of powder blending speeds, require less blending time before coalescence of the aqueous phase, resulting in increased density. Conversely lowr batch blending speeds, irrespective of powder blending speeds require longer blending times before coalescence and increased density results.

(d) The blending speed of the powder phase is interesting. At 5% Tullanox 500, the blending time prior to coalescence is a function of the batch blending speed, irrespective of the blending speed of the powder phase. At 4% Tullanox 500, the high blending speed of the powder phase with low blending speeds of the batch result in a more stable configuration requiring a longer blending time before coalescence. The reason for this is that the higher powder blending speed incorporates additional air into the 4% Tullanox powder phase which stabilizes the system when blended at low speed. Low powder blending speed at the 4% Tullanox 500 level may actually promote particle agglomeration and/or air elimination which becomes evident at low batch blending speeds; at high batch blending speeds no difference is detected between low or high speed powder blending. At 6% Tullanox 500, the reverse trend is visible for both high and low batch blending, i.e., low powder blending variations are more stable than high powder blending variations.

(2) Aerosil 972

High speed blending, irrespective of the blending intensity of the powder phase results in a shorter processing time than low speed batch mixing, with no differences in processing time due to the powder mixing intensity.

Data has indicated that for any given concentration of hydrophobic silica, the most stable systems, in decreasing order, are as follows:

Tullanox 500
Aerosil R 972
QUSO WR 50
QUSO WR 82

As can be seen, mixing conditions are a factor in determining the shear potential for any given system.

Generally the educator or dip tube should be of sufficient area to allow the bulk to flow unimpeded through the valve without bridging or compaction. The balance between the terminal and vapor port orifices as well as their absolute dimensions (all other factors being equal) control the delivery rate, the particle size and its density as the product emerges from the valve and thus the application characteristics. The entire phenomenon is based on shear.

It is apparent that if the vapor port is relatively large in respect to the terminal orifice, the amount of air admixed with the bulk in the valve housing will be proportionately high resulting in a low delivery rate.

It is also apparent that the shear potential or resistance of the bulk to shear and the actual shear through the valve must be carefully balanced to provide the properties demanded of the product. Further, if the spray is to be converted to a cream by rubbing, this factor must also be integrated into the shear equation. To increase the delivery rate and still retain the same application characteristics, the terminal orifice must be enlarged, adjusting the vapor port and shear potential of the bulk to provide the shear which will result in the desired delivery rate, spray pattern, dryness, creaminess, etc.

Typical diameters for the diameters of the outlet orifice, dip tube and vapor ports are:

| | |
|---|---|
| Terminal orifice | .020-.125 inch |
| Vapor port | .015-.080 inch |
| Internal diameter of dip tube | .030-.110 inch |

Such an orifice diameter permits the dispension of particles of a size range of from 0.5 to 100 microns or larger in flight or no later than reaching the target area.

The shear potential or resistance of the system is an aggregate of the entire shear experienced during passage through the terminal orifice resulting in partial coalescence of the aqueous phase, the further shearing of the bulk by rubbing on the skin causing additional coalescence.

The elegance and function of the lotions and creams (from the "powdery substance") for cosmetic and pharmaceutical applications are enhanced by the incorporation of non-system affecting materials in the concentrations generally used for the purposes indicated. These materials include well tolerated humectant polyols such as glycerin, propylene glycol and sorbitol; sun screening agents such as para-aminobenzoic acid and other benzoate and cinnamate derivatives; deodorant chemicals such as formaldehyde donor compounds and halogenated phenyl and other aromatic derivatives; antiperspirant chemicals such as aluminum and zirconium salts; therapeutic substances including steroids and antibiotics; pigments of the type normally used for make-up item such as for face powders, lipsticks, eyeshadows and rouges; cleansing surfactants of the anionic, nonionic and amphoteric types including ethoxylated phenoxyphenol derivatives, alkyl sulfate salts and the imidazolinium derivatives; viscosity modifying agents including polyvinyl pyrolidone, water soluble acrylate and cellulose polymers and natural gums including guar, alginate and carraghenates; and emollient, conditioning and modifying agents including ethoxylated and propoxylated fatty esters, sucrose fatty esters, lanolin derivatives and cationic polymers normally used to condition the hair and skin. Metallic fatty esters such as aluminum, magnesium, calcium and zinc stearates are useful to improve adhesion to the skin. Starches and fine talcs may be incorporated in the system to improve the feel of the product on the skin. Fragrance and color may be added as desired.

System affecting additives include oils, solvents and surfactants. Generally, chemicals with a high hydrogen bonding capability are better tolerated by the system than intermediate to low hydrogen bonding chemicals. Thus, for solvents, ethanol, glycerol or propylene glycol are better tolerated than xylenol or chlorinated solvents; for surfactants, linear alkyl sulfates are better tolerated than ethoxylated fatty acids although when the ethoxylate is the predominant portion of the molecule (such as PEG 2000 stearate) the surfactant becomes less oleophylic and is better tolerated by the system. Virtually all oils have a profound effect on the system. The mechanism involves the wetting out of the hydrophobic metal oxide resulting in the displacement of air and the collapse of the system. System affecting additives, such as lipids, may, however, be introduced into the system by dispersing in the aqueous phase as an oil-in-water emulsion. Thus, it can be seen that controlled destabilization resulting in the desired degree of shear when the bulk passes through the valve can be obtained by the judicious addition of relatively non-hydrogen bonding solvents, surfactants and lipids; these materials may contribute to humectancy, creaminess and elegance of application.

The basic system is extremely hydrophobic notwithstanding the fact that it can contain as much as 90% water. The system notwithstanding the water content assumes the properties of the hydrophobic metal oxide. Hydrophobicity is highly desirable in many products, including make-up items and certain topical pharmaceuticals to provide long term protection while resisting wash-off by the elements and body fluids or to protect the affected areas from moisture and provide a protective, controlled release matrix for the actives. The degree of hydrophobicity can be altered by modifying the hydrophobic interface. When the cohesive forces of the continuous hydrophobic barrier are reduced or interrupted, the bulk becomes more shear sensitive, the degree of coalescence and breakdown of the aqueous phase being a function of the intensity of shear as the bulk passes through the valve orifice plus any subsequent scrubbing action on the skin.

The water sensitivity can also be controlled by controlling the hydrophile-liphophile balance of the system, or by the introduction of hydrophyllic components such as hydrophyllic hydrocolloids or hydrophyllic metal oxides in sufficient quantity to disrupt the continuity of the hydrophobic metal oxide and provide the desired degree of hydrophyllicity.

A very particular application of the system of the invention is in the dispensing of an antiperspirant. A suitable general formulation follows:

| Ingredient | Amount, % W/W |
|---|---|
| Antiperspirant | 5-45 |
| Hydrophobic silica | 3-10 |
| Metal stearate | 0-5 |
| Water | 30-80 |
| Shear controlling agent, e.g., ethanol or surfactant | 0-5 |

Other additives such as talc or insoluble starch can be added to the formulation in amounts up to 25%, preferably 5 to 15%.

Dispensing of antiperspirant is one of the primary applications of the system of the invention. The U.S. Department of Health, Education and Welfare has published a monograph on antiperspirant products for human use. Most of the active antiperspirants are aluminum halides or complexes thereof. Representative antiperspirants that can be utilized in the dispensing system of this invention are:

Aluminum bromohydrate
Aluminum dichlorohydrate
Aluminum chlorohydrex PG
Aluminum dichlorohydrex PG
Aluminum sesquichlorohydrex PEG
Aluminum chloride
Aluminum zirconium chlorohydrates
Aluminum zirconium trichlorohydrate
Aluminum zirconium trichlorohydrex
Aluminum zirconium pentachlorohydrate
Aluminum zirconium pentachlorohydrex Gly
Aluminum zirconium tetrachlorohydrate
Aluminum zirconium tetrachlorohydrex Gly
Aluminum zirconium octachlorohydrate
Aluminum zirconium octachlorohydrex Gly
Aluminum chlorohydrate
Aluminum sesquichlorohydrate
Aluminum sesquichlorohydrex PG
Aluminum chlorohydrex PEG
Aluminum dichlorohydrex PEG
Aluminum sulfate
Buffered aluminum sulfate
Potassium aluminum sulfate Sodium aluminum chlorohydroxy lactate The antiperspirant material may be incorporated into the formulation either as a solid or in solution. In the former case, the stearate and the hydrophobic silica are blended together with the solid antiperspirant and this is then fed into a vortex of a mixer containing water and any optional material which may be dissolved therein. In the latter case, the preformed blend of stearate and hydrophobic silica is fed into the vortex of a mixer containing in the aqueous phase a suspension or solution of the antiperspirant material plus any optional materials to be incorporated in the aqueous phase. If desired, the antiperspirant may be incorporated in the interal aqueous phase or in the external powder phase or in both phases.

EXAMPLE 2

Formulations were prepared in accordance with the following table in which all ingredients are present in a % w/w basis. Each of the ingredients 2, 4, 6 and 7 when present in a particular formulation were premixed. A similar premixing of ingredients 1, 3 and 5 which were to be employed in a particular formulation was also effected.

Thereafter, the two premixes were blended by adding the solid mix to the vortex of the liquid mix in a high speed blender for from 5 to 10 seconds.

Samples 142 through 148 all sprayed with a fine to medium-coarse particle size using a valve of the following functional specifications:

| | |
|---|---|
| Terminal orifice | 0.040 inches |
| Vapor port | 0.030 inches |
| Internal diameter of dip tube | 0.060 inches |

TABLE 3

| | Sample Number | 142 | 143 | 144 | 145 | 146 | 147 | 148 |
|---|---|---|---|---|---|---|---|---|
| (1) | Zinc Stearate | 4.0 | 4.0 | 4.0 | 4.0 | 4.0 | 4.0 | 4.0 |
| (2) | Anhydrous Alcohol SDA 40 | — | — | — | — | 5.0 | — | — |
| (3) | Hydrophobic Silica* | 6.0 | 6.0 | 6.0 | 6.0 | 6.0 | 6.0 | 6.0 |
| (4) | Glycerin | 15.0 | 15.0 | 15.0 | — | — | — | — |
| (5) | Aluminum Chlorhydroxide, Impalpable Powder | 45.0 | — | 15.0 | — | — | 18.75 | 45 |
| (6) | Aluminum Chlorhydroxide, 50% aqueous solutions | — | 75.0 | 60.0 | 75.0 | 75.0 | 37.5 | — |
| (7) | Water | 30.0 | — | — | 15.0 | 10.0 | 33.75 | 45.0 |
| (8) | Tapped Density | .49 | .56 | .52 | .51 | .55 | .50 | .52 |

*The hydrophobic silica used is produced by Degussa Incorporated, Tulco Incorporated and Philadelphia Quartz Company.

Samples with lower densities exhibit finer sprays than do samples with higher densities. Sample 146 with 5% of anhydrous alcohol exhibits the largest particle size, the alcohol exerting a destabilizing effect on the system when in a state of shear, i.e., as it is passing through the valve. All samples deposit as a metastable powder which rubs out into a creamy application and dries within a few seconds to a non-sticky or non-tacky astringent residue.

| | | % W/W |
|---|---|---|
| (1) | Aluminum chlorhydroxide, Macrospherical ®95[1] | 25.0 |
| (2) | Zinc stearate | 4.0 |
| (3) | Hydrophobic silica (Tullanox 500)[2] | 4.0 |
| (4) | Water | 67.0 |
| | $H_2O$/Tullanox 500 | 11.5/1 |

Processing instructions (A) Mix (1), (2) and (3)
(B) Add (4) to (A) with high intensity blending or,
(C) Add (4) to (A) and then subject to high intensity blending.

Figure 4:
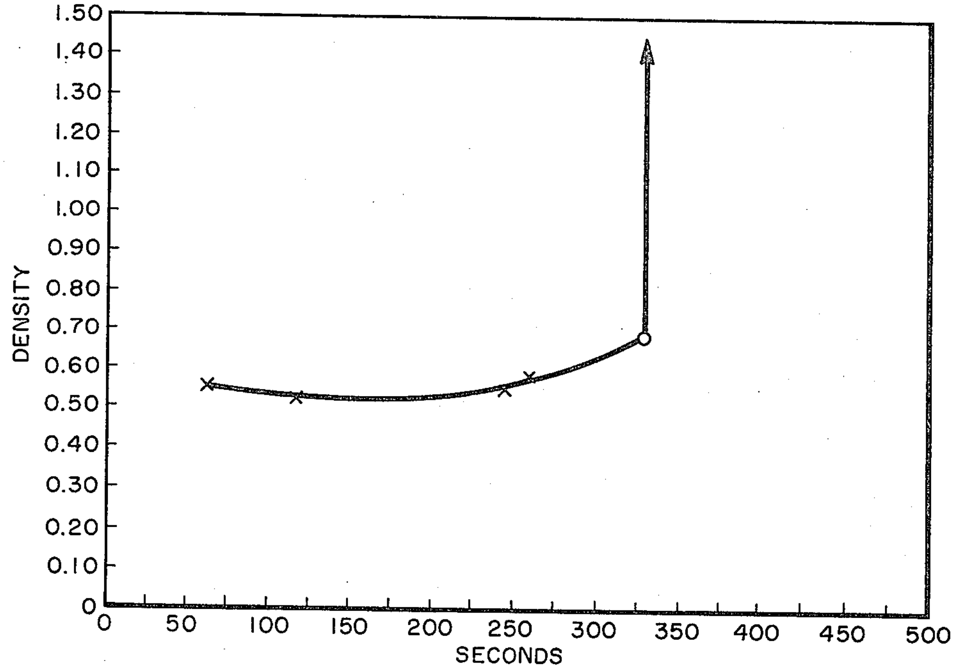
FIG. 4 is a graph of mixing time vs. density of a typical example of the bulk suspension of this invention.

[1]Product of Reheis Chemical Company comprising hollow spheres with an apparent density of 0.86 g/cc.
[2]Tulco, Incorporated Blending time vs. density is shown in FIG. 4.

High speed blending of the formula illustrated in Example 3 for 65, 120 and 240 seconds resulted in densities of 0.53–0.55 g/cc or, for practical purposes, a straight line with the same degree of coalescence occurring on the flat portion of the curve. With additional high speed blending imparted to the formula, the aqueous-air suspension collapses into a totally coalesced, creamy, aerated substance after about 330 seconds. This is an extremely sharp, repeatable end point. To verify the lack of physical change in the flat portion of the curve, samples from the above three blending periods were evaluated with the following results. See Table 4 which follows.

A verifiable, repeatable, qualitatively-quantitative test was developed to measure the effect of shear on the pre- and post-dispensed samples. The bulk/spray shear ratio test involves the placement of equivalent amounts of the pre- and post-dispensed samples on the inside of the forearm and finger rubbing the same until coalescence occurs. The number of individual rubs of the pre- and post-samples to achieve coalescence are noted and are also expressed as a pre/post shear ratio.

TABLE 4

| Blending Time | Density | Valve Terminal Orifice/Vapor Port/ Dip Tube i.d. | Delivery Rate/Spray | Bulk/Spray Pre/Post Rubout | Shear Ratio Pre/Post Ratio |
|---|---|---|---|---|---|
| 65 sec. | 0.55 g/cc | .050/.030/.090 inches | 140 mg | 13/9 | 1.4/1 |
| 120 sec. | 0.53 g/cc | .050/.030/.090 inches | 140 mg | 12/9 | 1.3/1 |
| 240 sec. | 0.55 g/cc | .050/.030/.090 inches | 140 mg | 12/9 | 1.3/1 |

The three samples blended at 65, 120 and 240 seconds illustrated in FIG. 4 and Table 4 sprayed satisfactorily with good skin coverage and adhesion. The sprayed particles were medium size by visual analysis. There were no differences among the three samples, all three exhibiting the same spray characteristics, valve function and shear.

Table 5 which follows shows that increased density (coalescence) occurs with additional high intensity mixing. Skin coverage and adhesion were satisfactory for both the 255 and 260 second samples. Both samples sprayed satisfactory.

TABLE 5

| Blending Time | Density | Valve Terminal Orifice/Vapor Port/ Dip Tube i.d. | Delivery Rate/Spray | Bulk Spray Pre/Post Rubout | Shear Ratio Pre/Post Ratio |
|---|---|---|---|---|---|
| 255 sec. | 0.58 g/cc | .050/.030/.090 inches | 150 mg | 9/3 | 3.0/1 |
| | | .060/.050/.090 inches | 160 mg | 10/5 | 2.0/1 |
| 260 sec. | 0.63 g/cc | .050/.030/.090 inches | 160 mg | 6/3 | 2.0/1 |
| 330 sec. | 0.68 g/cc | aerated coalesced cream, not usable in this invention. | | | |

Video tapes of controls (unsprayed bulk) versus three sprayed samples each of 0.53 and 0.58 g/cc density bulks representing varying degrees of shear were prepared. The material was applied to a slide and the image reconstructed using laser light onto a TV monitor for viewing the particle images at 325× magnification. A probe was used to disturb the field while viewing the results on the monitor. Initial qualitative probes indicated an almost straight line relationship between the degree of shear and coalescence. The samples tested are detailed in Table 6.

TABLE 6

| Sample | Terminal Orifice | Vapor Tap | ID Dip Tube | Spray Rate/ Squeeze (mg) | Shear |
|---|---|---|---|---|---|
| | (Thousanths of an Inch) | | | | |
| A. Density 0.53 | | | | | |
| 6 | .080 | .050 | .090 | 280 | minimal |
| 7 | .060 | .050 | .090 | 160 | intermediate |
| 12 | .040 | .050 | .090 | 40 | high |
| B. Density 0.58 | | | | | |
| 10 | 70 | 30 | 90 | 280 | minimal |
| 9 | 40 | 30 | 90 | 100 | intermediate |
| 11 | 40 | 50 | 90 | 40 | high |
| C. Control | | | | | |
| Bulks, 0.53 and 0.58 densities, non sheared | | | | | |

Dry air was bubbled through a test tube containing the unsheared control bulk. When a probe was applied to a large aggomerate on the slide, the agglomerate on the slide flew apart without any indication of coalescence. This was clearly visible on the TV monitor. The large agglomerates appeared to be held together by electrostatic forces and were strongly attached to the probe.

Initial tests verified the hypothesis that no visual coalescence occurred with unsheared control samples whereas coalescence appeared to be a straight line function of shear. Preliminary data indicate a mass median diameter of 18 microns for the 0.58 density control sample (unsheared material) and 190 microns for sample No. 9 (Table 6) for the sheared material using laser holography techniques for particle size measurements.

Samples of the antiperspirant formulation of Example 3 having a density of 0.58 g/cc were sprayed through valve systems imparting different levels of shear to the formulations. The sprayed particles were subjected to particle size analysis using laser holography. The results follow:

TABLE 7

| Shear | = or > | % By Mass 11.3 microns |
|---|---|---|
| None | | 22.0 |
| Medium | | 0.8 |
| High | | 0.3 |

Thus, there was about 700% reduction of the mass of particles less than 11.4 microns for the high sheared sample as compared to the non-sheared sample.

Variations in delivery rate for the 0.58 density material are provided in the following table.

TABLE 8

| Terminal orifice/ vapor tap/I.D. dip tube (TO/VT/DT) | Delivery Rate, mg/spray |
|---|---|
| .060/.040/.060 inches | 160 |
| .070/.050/.090 inches | 200 |
| .050/.040/.060 inches | 160 |
| .080/.040/.060 inches | 220 |
| .040/.050/.060 inches | 40 |
| .050/.050/.090 inches | 100 |

The following additional formulations were prepared and evaluated:

EXAMPLE 4

Antiperspirant Spray

| | % W/W |
|---|---|
| (1) Aluminum chlorhydrate, Microdi ®[1] | 50.0 |
| (2) Hydrophobic silica (Tullanox 500) | 4.0 |
| (3) Water | 46.0 |
| $H_2O$/Tullanox 500 | 11.5/1 |

Processing instructions:

(A) Mix (1) and (2)
(B) Add (3) and (A) with high intensity mixing or,
(C) Add (3) to (A) and then subject to high intensity, mixing.

[1]Product of Reheis Chemical with an apparent density of 0.63 g/cc.

The density of the bulk just prior to collapse after 497 seconds of continuous high intensity blending was 0.74. The delivery rate using a 0.060/0.050/0.090 TD/VT/DT valve was 150 mg/spray and the pre/post shear rub-outs and ratio were 3/2 and 1.5/1 respectively. The application was adherent and uniform and dried to a non tacky, non sticky residue in about 15 seconds. The product sprayed with visible coalescence. For comparative purposes a 25% aqueous solution of aluminum chloroxide applied to the skin in the same manner as the above sample becomes tacky in about 90 seconds and dries out in about 160 seconds.

EXAMPLE 5

Antiperspirant Spray

| | % W/W |
|---|---|
| Aluminum chlorhydrate (micronized impalpable powder) | 50 |
| Hydrophobic silica (QUSO 50) | 3 |
| Water | 47 |
| $H_2O$/QUSO 50 | 15.66/1 |

Processing instructions: same as for Example 4 but high intensive blending time was 5 seconds which resulted in a density of 0.93 g/cc. The delivery rate was 300 mg/spray using a 0.060/0.040/0.090 valve. The pre/post shear rub-outs and ratio were 3/2 and 1.5/1 respectively. The sample applied as a creamy application to the skin.

EXAMPLE 6

Pigment Base Formulation

| | | % W/W |
|---|---|---|
| (1) | Titanium dioxide (water dispersible, apparent density of 0.96) | 50 |
| (2) | Hydrophobic silica (Tullanox 500) | 4 |
| (3) | Water | 46 |
| | $H_2O$/Tullanox 500 | 11.5/1 |

Processing instructions:
(A) Mix (1) and (2)
(B) Add (3) to (A) with high intensity blending or,
(C) Add (3) to (A) and then subject to high intensity blending.

After 60 seconds of intermittent high intensity blending the density of the bulk was 1.05 g/cc. The density after 37 seconds of intermittent high intensity was 0.77 g/cc.

EXAMPLE 7

Pigment Base Formulation

| | | % W/W |
|---|---|---|
| (1) | Titanium dioxide (water dispersible, apparent density of 0.96) | 50 |
| (2) | Hydrophobic silica (Tullanox 500) | 3 |
| (3) | Water | 47 |
| | $H_2O$/Tullanox 500 | 11.7/1 |

Processing instructions: same as for Example 6. After 5 seconds of high intensity blending, the density was 0.86 g/cc. The delivery rate was 220 mg/spray using a 0.060/0.050/0.090 valve. The pre/post shear rub-out and ratio were 6/3 and 2/1 respectively.

EXAMPLE 8

Pigment Base Formulation

| | | % W/W |
|---|---|---|
| (1) | Titanium dioxide (water dispersible, apparent density of 0.96) | 50 |
| (2) | QUSO 50 | 4 |
| (3) | Water | 46 |
| | $H_2O$/QUSO 50 | 11.5/1 |

Processing instructions: same as for Example 6. After 30 seconds of high intensity blending the density was 1.00 g/cc and the delivery rate was 240 mg/spray using a 0.060/0.050/0.090 valve. The pre/post shear rub-out and ratio were both 3/1.

EXAMPLE 9

Pigment Base Formulation

| | | % W/W |
|---|---|---|
| (1) | Titanium dioxide | 50 |
| (2) | QUSO 50 | 5 |
| (3) | Water | 45 |
| | $H_2O$/QUSO 50 | 9/1 |

Processing instructions: same as Example 6.

After 10 seconds of high intensity blending the density was 0.99 g/cc and the delivery rate was 230 mg/spray using a 0.060/0.050/0.090 valve. The pre/post shear rub-out and ratio were both 2/1.

A density range useful in our technology from about 0.3 to 1.5 g/cc appears feasible. If a material such as barium sulfate were used in a high concentration the density of the air emulsion would undoubtedly be in the area of 1.5 g/cc or greater.

The above Examples 6–9 inclusive illustrate relatively high density systems due to inclusion of ingredients such as titanium dioxide which have a high density. Formulations of even higher density could be formulated with higher density additives such as barium sulfate.

An antiperspirant formulation was prepared having increased shear sensitivity by including a controlled amount of insoluble hydrophobic starch as a shear affecting additive.

EXAMPLE 10

| Ingredient | % W/W |
|---|---|
| Aluminum Chlorohydroxide, Macrospherical 95 | 25 |
| Tullanox 500 | 4.0 |
| Insoluble, hydrophobic starch | 10 |
| Water | 61 |

The preblended dry ingredients and water mixed for 10 seconds had a density of 0.61 g/cc and a delivery rate of 140 mg/spray through a valve system having the following orifices: TO/VT/DT=0.050/0.040/0.090. The pre/post shear rub-out and ratio were both 15/1.

Amount of Actives per Application

The actives of several formulations, their delivery rates, amounts of actives delivered, etc., are detailed in Table 9 which follows:

TABLE 9

| Sample No. | % Aluminum Chlorhydroxide in Formula | Delivery Rate Per Spray (mg) | Amount Aluminum Chlorhydroxide Delivered/Spray (mg) |
|---|---|---|---|
| 6 | 25 | 280 | 70.0 |
| 7 | 25 | 160 | 42.5 |
| 12 | 25 | 40 | 10.0 |
| 13 | 25 | 150 | 37.5 |

The usual amount of aluminum chlorhydroxide deposited per application in each axilla generally ranges from about 60-80 mg. Thus, Sample 6, Table 9, will deliver an effective quantity of antiperspirant salt with one spray. Samples 7 and 13 will deliver effective quantities with two sprays. There is sufficient flexibility in the system to allow for varying concentrations and types of antiperspirant salts to achieve the desired efficacy in the dose/response curve.

Examples of other actives which can be dispensed in the system of the invention follow.

EXAMPLE 11

Insecticide Spray

| | | % W/W |
|---|---|---|
| (1) | Trichlorfon[1] | 0.5-1.0 |
| (2) | Hydrophobic silica (Aerosil R 972) | 3.0-7.0 |
| (3) | Water | q.s. to 100 |

Processing instructions (A) Mix (1) and (2)
(B) Add (3) to (A) with high intensity blending or,
(C) Add (3) to (A) and then subject to high intensity blending.

[1]o,o-dimethyl (2,2,2,-trichlor-1-hydroxyethyl) phosphonate

EXAMPLE 12

Hard Surfactant Disinfectant

| | | General | Example |
|---|---|---|---|
| | | % W/W | |
| (1) | Diisobutylphenoxyethoxyethyl dimethyl benzyl ammonium chloride monohydrate (Hyamine 1622) | 0.10-0.25 | 0.1 |
| (2) | Alkylphenoxy polyethoxy ethanol (Triton X 100) | 1.0-5.0 | 1.0 |
| (3) | Hydrophobic silica (Tullanox 500) | 3.0-12 | 10.0 |
| (4) | Glycerin | 0-15 | — |
| (5) | Water | q.s. to 100 | q.s. to 100 |
| | $H_2O$/Tullanox 500 | | 8.89/1 |

Processing instructions:

(A) Mix (1) and (3)
(B) Mix (2), (4) and (5)
(C) Add (a) and (B) together and subject to low intensity blending.

After 5 seconds of low intensity blending the density was 0.37 g/cc and the delivery rate was 210 mg/spray using a 0.050/0.040/0.090 valve. The pre/post shear rub-out and ratio were both 50+/1. The product sprays out in liquid droplets.

EXAMPLE 13

Room Deodorant—Illustrating Addition of Active Material to Preformed Air Emulsion

| | | General | Example |
|---|---|---|---|
| | | % W/W | |
| (1) | Spray dried fragrance (In-Cap Powder Bqt. DPR 267-145 Polak's Frutal Works) | 0.1-1.0 | 1 |
| (2) | Hydrophobic silica (Tullanox 500) | 3.0-10.0 | 7 |
| (3) | Water | q.s. to 100 | 92 |
| | $H_2O$/Tullanox 500 | | 13.14/1 |

Processing instructions:

(A) Mix (2) and (3) and blend using a high intensity blending for 30 seconds.
(B) Add (1) and blend using low intensity blending for 2 seconds.

The density of the bulk prepared as above was 0.40 g/cc and the delivery rate was 144 mg/spray using a 0.060/0.050/0.090 valve. The pre/post shear rub-out and ratio were both 4/1.

EXAMPLE 14

Antiperspirant with Hydrophobic Titanium Dioxide[1]

| | | % W/W |
|---|---|---|
| (1) | Aluminum chlorhydroxide (Macrospherical 95)[2] | 25.0 |
| (2) | Zinc stearate | 4.0 |
| (3) | Hydrophobic titanium dioxide | 4.0 |
| (4) | Water | 67.0 |
| | $H_2O$/Hydrophobic $TiO_2$ | 16.8/1 |

[1]Degussa Incorporated
[2]Impalpable microspheres, 95% > 10 microns

Processing instructions: identical to previous batches.

The bulk collapsed after 5 seconds of high intensity blending. After 3 seconds of low intensity blending the density was 0.73 g/cc and the delivery rate was 210 mg/spray using a 0.060/0.050/0.090 valve. The pre/-post shear rub-out and ratio were both 6/1.

On a blender with 14 speeds: high intensity is a setting of 13 and low intensity is a setting of 2.

EXAMPLE 15

Antiperspirant with Hydrophobic Silica, Aerosil R 927 (Degussa)

| | | % W/W |
|---|---|---|
| (1) | Aluminum chlorhydroxide (Macrospherical 95) | 25.0 |
| (2) | Zinc oxide | 4.0 |
| (3) | Hydrophobic silica (Aerosil R 972) | 4.0 |
| (4) | Water | 67.0 |
| | $H_2O$/Aerosil R 972 | 16.8/1 |

Processing instructions: identical to previous batches.

After 5 seconds of high intensity blending the density was 0.49 g/cc and the delivery rate was 280 mg/spray using a 0.060/0.040/0.090 valve. The pre/post shear rub-out and ratio were 15/12 and 1.3/1, respectively.

EXAMPLE 16

Formulation to illustrate the difference in pre and post shearing (see also Example 10, this Section).

| | % W/w |
|---|---|
| (1) Tullanox T 500 | 10 |
| (2) Water | 90 |
| $H_2O$/Tullanox T 500 | 9/1 |

Processing instructions: The components were blended together for 10 seconds using high intensity blending. The density of the bulk was 0.34 g/cc and the delivery rate of the system was 240 mg/spray using a 0.040/0.010/0.090 valve. The pre-post shear rub-out and ratio were both 50+/1.

The system of the present invention also provides a convenient way for dispensing water and air labile bioactive materials. For example, hydrogen peroxide may conveniently be reduced into powder form and dispensed by the system of the invention as required. Other sensitive bioactive materials amenable to stabilization using my invention include certain pesticides, antibiotics, photosensitive materials, oxidizing and reducing agents and the like.

EXAMPLE 17

8.6 parts by weight 35% hydrogen peroxide were mixed with 81.4 parts by weight water. 10.0 parts by weight hydrophobic silica were added to the vortex of the aqueous mixture using high intensity mixing to produce a product of density 0.33 g/cc.

The product containing 3% $H_2O_2$ dispenses as a spray using the same valve as described under Example 2.

When alcoholic potassium hydroxide and isopropyl myristate (to break the system) were added to a small portion of Example 3 in a glass bottle, pressure was noted after a few seconds. The system continued to evolve oxygen for a period greater than one hour.

Examples of packaged systems requiring separation of incompatible materials that can be compatibly formulated in the two phase system of the invention are:

1. An exothermic reaction resulting from the liberation of redox chemicals when the bulk is sheared through the valve such as hydrogen peroxide effectively separated from a reducing agent such as sodium thiosulfate.

2. An endothermic reaction based on the hydration of certain salts.

3. Oxidation hair dyes based on hydrogen peroxide and dyes such as paraphenylenediamine dyes leading to a one step, no mixing, no spillage product. The chemicals are released by combing (shear) the product through the hair.

4. Foaming cosmetic cleanser containing baking soda and citric acid. When applied to the skin and rubbed out produces an effervescent creaminess which floats away the soil and conditions the skin.

5. Enzyme and activator as a stain remover activated by rubbing onto the stain.

The system of the invention can also be utilized for the controlled release of agents such as disinfectants and deoderants, e.g., hypochlorites spray dispensed into a toilet. The product will resist several flushings while releasing the active ingredients over prolonged periods of time.

The system can also be utilized to stabilize air and ultraviolet sensitive materials such as hydrogen peroxides, hypochlorites, certain antibiotics and other therapeutic agents and certain pesticides including pyrethrin, pH sensitive materials such a stain removing enzymes or proteolytic enzymes such as keratinase useful as a depilatory, where the pH activator is released on shear.

Thus, the invention demonstrates the use of shear to provide products of varying properties from powdery particles to creamy applications. During processing of the bulk sufficient energy is added by high speed mixing to render the bulk shear sensitive so that on passage through an outlet orifice of preselected diameter a controlled amount of destabilization and coalescence occurs. The orifice is sized to impart an amount of shear effective to at least partially destabilize the interfacial barrier. At the point of total coalescence the barrier is destroyed and the internal, discontinuous water phase becomes an external continuous phase. At coalescence the hydrophobic metal oxide appears to impart water resistance to the surface of the target such as the skin of the user. The delivery rate can be varied over wide ranges from 40 to 300 mg per spray usually 60 to 200 mg/spray. p It is to be realized that only preferred embodiments of the invention have been described and that numerous substitutions, modifications and alterations are permissible without departing from the spirit and scope of the invention as defined in the following claims.

I claim:

1. A system for dispensing a material to a target comprising in combination:
a container including;
a compartment within the container receiving a body of a water-in-air suspension comprising fine droplets of water stabilized by an interfacial barrier of very fine hydrophobic metal oxide particles as a first phase and air as a second phase, said material being present in either of said phases;
a terminal orifice capable of applying a preselected shear to said suspension in an amount effective to at least partially destabilize the suspension and cause coalescence of said droplets;
means communicating the compartment with the outlet orifice; and
means for propelling the suspension through the orifice toward the target.

2. A system according to claim 1 in which the propelling means includes means for generating a pulse of gas.

3. A system according to claim 2 in which the propelling means includes container deformable portions surrounding said compartment.

4. A system according to claim 3 in which the generating means includes means for introducing ambient air into container through said orifice.

5. A system according to claim 4 in which said introducing means includes headspace in said container for receiving ambient air through said orifice.

6. A system according to claim 5 in which said container further includes walls defining a mixing chamber in communication with the headspace, suspension compartment and outlet orifice.

7. A system according to claim 6 in which the mixing chamber communicates with the headspace through a port in said wall and with the compartment through a dip tube and the outlet orifice has a diameter from 0.020 to 0.125 inches, the port has a diameter from 0.015 to 0.080 inches and the dip tube has an internal diameter from 0.030 to 0.110 inches.

8. A system according to claim 7 in which, the suspension contains in parts by weight:

25% to 98.9% of aqueous liquid;

1% to 15% hydrophobic metal oxide;

0.1% to 60% dispensible material.

9. A system according to claim 8 in which the dispensible material is contained in the liquid phase and/or external air phase.

10. A system according to claim 9 in which the density of the suspension is from 0.3 to 1.5 g/cc.

11. A System according to claim 10 in which the density is from 0.45 to 0.90 g/cc.

12. A system according to claim 10 in which the hydrophobic metal oxide is selected from silicon, titanum, aluminum, zirconum, vanadium, iron or mixtures thereof.

13. A system according to claim 12 in which the hydrophobic oxide is silane treated.

14. A system according to claim 13 in which the silane treated hydrophobic metal oxide is selected from compounds of the formula: $eO—MR_aX_b$ where e is the oxide surface, O is oxygen, M is a metal, R is selected from alkyl, aryl, arylalkyl, alkoxy, X is halogen or hydroxyl a is a number from 1 to 3, b is 0 or a number from 1 to 2 and the sum of a+b is 3.

15. A system according to claim 14 in which M is silicon.

16. A system according to claim 15 in which the hydrophobic metal oxide is a pyrogenic silica.

17. A system according to claim 16 in which the silica contains at least 0.5% by weight organic groups.

18. A system according to claim 10 in which the ratio of hydrophobic metal oxide to aqueous liquid is from 1 to 50/1.

19. A system according to claim 18 in which the ratio is from 2 to 15/1.

20. A system according to claim 18 in which the dispensible material is an antiperspirant powder present in the external air phase.

21. A system according to claim 20 in which the antiperspirant powder is present in an amount from 5% to 45% by weight, the hydrophobic metal oxide is in an amount from 3 to 10% by weight, water is present in an amount from 30 to 80% by weight and further including from 0 to 5% by weight of a metal stearate and 0 to 5% of a shear control agent.

22. A system according to claim 21 in which the antiperspirant powder is an aluminum-halogen compound having at least one Al-halo bond.

23. A system according to claim 22 in which the hydrophobic metal oxide is silica, the metal stearate is zinc stearate and the shear control agent is ethanol.

* * * * *

UNITED STATES PATENT AND TRADEMARK OFFICE

CERTIFICATE OF CORRECTION

PATENT NO. : 4278206

DATED : July 14, 1981

INVENTOR(S) : Samuel Prussin

It is certified that error appears in the above-identified patent and that said Letters Patent are hereby corrected as shown below:

Column 2, line 1, change "produce" to --product--

Column 9, line 62, correct "lower"

Column 16, line 46, correct "Microdri"

Column 22, line 22, cancel "p"

Signed and Sealed this

***Twentieth* Day of *October 1981***

[SEAL]

*Attest:*

GERALD J. MOSSINGHOFF

*Attesting Officer* *Commissioner of Patents and Trademarks*